(12) United States Patent
Brocker et al.

(10) Patent No.: US 9,180,030 B2
(45) Date of Patent: Nov. 10, 2015

(54) LOW PROFILE NON-SYMMETRICAL STENT

(75) Inventors: David Brocker, Carmel, IN (US);
William K. Dierking, Louisville, KY (US); Alan R. Leewood, Lafayette, IN (US); Timothy A. M. Chuter, San Francisco, CA (US); Blayne A. Roeder, Lafayette, IN (US); Steven J. Charlebois, West Lafayette, IN (US); Richard A. Swift, South Bend, IN (US); Sharath Gopalakrishnamurthy, Bangalore (IN); Matthew S. Huser, West Lafayette, IN (US); Jarin Kratzberg, Lafayette, IN (US); Erik E. Rasmussen, Slagelse (DK); Bent Oehlenschlaeger, Skensved (DK); Kim Mogelvang Jensen, Copenhagen SV (DK)

(73) Assignee: Cook Medical Technologies LLC, Bloomington, IN (US)

( * ) Notice: Subject to any disclaimer, the term of this patent is extended or adjusted under 35 U.S.C. 154(b) by 842 days.

(21) Appl. No.: 12/332,904

(22) Filed: Dec. 11, 2008

(65) Prior Publication Data
US 2009/0171437 A1    Jul. 2, 2009

Related U.S. Application Data

(60) Provisional application No. 61/016,753, filed on Dec. 26, 2007.

(51) Int. Cl.
*A61F 2/06* (2013.01)
*A61F 2/86* (2013.01)
(Continued)

(52) U.S. Cl.
CPC . *A61F 2/86* (2013.01); *A61F 2/856* (2013.01);
*A61F 2/915* (2013.01); *A61F 2/07* (2013.01);
*A61F 2002/065* (2013.01);
(Continued)

(58) Field of Classification Search
CPC ........................................................ A61F 2/06
USPC ........................................................ 623/1.15
See application file for complete search history.

(56) References Cited

U.S. PATENT DOCUMENTS 5,258,021 A * 11/1993 Duran .......................... 623/2.36
5,292,331 A    3/1994 Boneau
(Continued)

FOREIGN PATENT DOCUMENTS

EP    0960607    1/1999
EP    0686379    8/2000
(Continued)

OTHER PUBLICATIONS

Office Action for U.S. Appl. No. 12/622,351 dated Oct. 6, 2010, 12 pgs.
(Continued)

*Primary Examiner* — Thomas J Sweet
*Assistant Examiner* — Matthew Schall
(74) *Attorney, Agent, or Firm* — Brinks Gilson & Lione

(57) ABSTRACT

A stent for use in a medical procedure having opposing sets of curved apices, where the curved section of one set of apices has a radius of curvature that is greater than the curved section of the other set of apices. One or more such stents may be attached to a graft material for use in endovascular treatment of, for example, aneurysm, thoracic dissection, or other body vessel condition.

20 Claims, 11 Drawing Sheets

(51) Int. Cl.
*A61F 2/856* (2013.01)
*A61F 2/915* (2013.01)
*A61F 2/07* (2013.01)
*A61F 2/848* (2013.01)

(52) U.S. Cl.
CPC .............. *A61F 2002/8486* (2013.01); *A61F 2002/91516* (2013.01); *A61F 2220/0016* (2013.01); *A61F 2220/0075* (2013.01); *A61F 2230/0013* (2013.01)

(56) References Cited

U.S. PATENT DOCUMENTS

| | | | |
|---|---|---|---|
| 5,403,341 A | 4/1995 | Solar | |
| 5,569,295 A | 10/1996 | Lam | |
| 5,607,468 A | 3/1997 | Rogers et al. | |
| 5,674,278 A | 10/1997 | Boneau | |
| 5,749,921 A | 5/1998 | Lenker et al. | |
| 5,843,164 A * | 12/1998 | Frantzen et al. | 623/1.16 |
| 5,906,639 A | 5/1999 | Rudnick et al. | |
| 5,913,897 A * | 6/1999 | Corso et al. | 623/1.15 |
| 5,961,546 A | 10/1999 | Robinson et al. | |
| 5,993,482 A | 11/1999 | Chuter | |
| 6,071,307 A * | 6/2000 | Rhee et al. | 623/1.13 |
| 6,110,198 A | 8/2000 | Fogarty et al. | |
| 6,203,569 B1 | 3/2001 | Wijay | |
| 6,245,102 B1 | 6/2001 | Jayaraman | |
| 6,296,662 B1 * | 10/2001 | Caffey | 623/2.18 |
| 6,336,937 B1 | 1/2002 | Vonesh et al. | |
| 6,346,118 B1 | 2/2002 | Baker et al. | |
| 6,348,068 B1 | 2/2002 | Campbell et al. | |
| 6,350,277 B1 | 2/2002 | Kocur | |
| 6,368,345 B1 | 4/2002 | Dehdashtian et al. | |
| 6,423,090 B1 * | 7/2002 | Hancock | 623/1.15 |
| 6,451,051 B2 | 9/2002 | Drasler et al. | |
| 6,471,722 B1 | 10/2002 | Inoue | |
| 6,514,282 B1 | 2/2003 | Inoue | |
| 6,524,335 B1 | 2/2003 | Hartley et al. | |
| 6,539,984 B2 * | 4/2003 | Lam | 140/71 R |
| 6,579,314 B1 | 6/2003 | Lombardi et al. | |
| 6,582,458 B1 | 6/2003 | White et al. | |
| 6,585,757 B1 | 7/2003 | Callol | |
| 6,592,614 B2 | 7/2003 | Lenker et al. | |
| 6,616,689 B1 | 9/2003 | Ainsworth et al. | |
| 6,629,994 B2 | 10/2003 | Gomez et al. | |
| 6,635,083 B1 | 10/2003 | Cheng et al. | |
| 6,645,242 B1 | 11/2003 | Quinn | |
| 6,648,911 B1 | 11/2003 | Sirhan et al. | |
| 6,663,661 B2 | 12/2003 | Boneau | |
| 6,673,102 B1 | 1/2004 | Vonesh et al. | |
| 6,695,875 B2 | 2/2004 | Stelter et al. | |
| 6,723,116 B2 | 4/2004 | Taheri | |
| 6,740,115 B2 | 5/2004 | Lombardi et al. | |
| 6,849,088 B2 * | 2/2005 | Dehdashtian et al. | 623/1.36 |
| 6,860,901 B1 | 3/2005 | Baker et al. | |
| 6,878,160 B2 | 4/2005 | Gilligan et al. | |
| 6,962,604 B2 * | 11/2005 | Hijlkema | 623/1.15 |
| 6,974,471 B2 | 12/2005 | Van Schie et al. | |
| 7,147,657 B2 | 12/2006 | Chiang et al. | |
| 7,186,263 B2 * | 3/2007 | Golds et al. | 623/1.13 |
| 7,232,459 B2 | 6/2007 | Greenberg et al. | |
| 7,264,632 B2 | 9/2007 | Wright et al. | |
| 7,279,003 B2 | 10/2007 | Berra et al. | |
| 7,318,835 B2 | 1/2008 | Berra | |
| 7,331,992 B2 | 2/2008 | Randall et al. | |
| 7,341,598 B2 | 3/2008 | Davidson et al. | |
| 7,407,509 B2 | 8/2008 | Greenberg et al. | |
| 7,473,275 B2 * | 1/2009 | Marquez | 623/2.38 |
| 7,534,258 B2 | 5/2009 | Gomez et al. | |
| 7,615,072 B2 | 11/2009 | Rust et al. | |
| 7,722,657 B2 | 5/2010 | Hartley | |
| 7,758,626 B2 | 7/2010 | Kim et al. | |
| 7,766,962 B1 | 8/2010 | Quinn | |
| 7,794,492 B2 | 9/2010 | Ishimaru et al. | |
| 7,828,837 B2 | 11/2010 | Khoury | |
| 7,887,580 B2 | 2/2011 | Randall et al. | |
| 7,927,363 B2 | 4/2011 | Perouse | |
| 8,043,354 B2 | 10/2011 | Greenberg et al. | |
| 8,128,678 B2 | 3/2012 | Leewood et al. | |
| 8,206,427 B1 | 6/2012 | Ryan et al. | |
| 8,292,943 B2 | 10/2012 | Berra et al. | |
| 8,333,799 B2 | 12/2012 | Bales et al. | |
| 8,348,994 B2 | 1/2013 | Leopold et al. | |
| 8,394,136 B2 | 3/2013 | Hartley et al. | |
| 8,425,586 B2 | 4/2013 | Leopold et al. | |
| 2001/0000188 A1 | 4/2001 | Lenker et al. | |
| 2002/0016627 A1 | 2/2002 | Golds | |
| 2002/0022877 A1 * | 2/2002 | Mueller et al. | 623/1.16 |
| 2002/0032487 A1 | 3/2002 | Dua et al. | |
| 2002/0143381 A1 | 10/2002 | Gilligan et al. | |
| 2002/0177890 A1 | 11/2002 | Lenker | |
| 2003/0033002 A1 | 2/2003 | Dehdashtian et al. | |
| 2003/0033003 A1 * | 2/2003 | Harrison et al. | 623/1.15 |
| 2003/0050684 A1 | 3/2003 | Abrams et al. | |
| 2003/0088305 A1 * | 5/2003 | Van Schie et al. | 623/1.12 |
| 2003/0120263 A1 | 6/2003 | Ouriel et al. | |
| 2003/0125797 A1 * | 7/2003 | Chobotov et al. | 623/1.13 |
| 2003/0130720 A1 | 7/2003 | DePalma et al. | |
| 2003/0199967 A1 | 10/2003 | Hartley et al. | |
| 2004/0002751 A1 | 1/2004 | Gilligan et al. | |
| 2004/0054396 A1 | 3/2004 | Hartley et al. | |
| 2004/0073289 A1 | 4/2004 | Hartley | |
| 2004/0093063 A1 | 5/2004 | Wright et al. | |
| 2004/0117003 A1 | 6/2004 | Ouriel et al. | |
| 2004/0117004 A1 * | 6/2004 | Osborne et al. | 623/1.36 |
| 2004/0215316 A1 | 10/2004 | Smalling | |
| 2004/0215319 A1 | 10/2004 | Berra et al. | |
| 2004/0254625 A1 * | 12/2004 | Stephens et al. | 623/1.1 |
| 2005/0033406 A1 | 2/2005 | Barnhart et al. | |
| 2005/0049674 A1 * | 3/2005 | Berra et al. | 623/1.13 |
| 2005/0090834 A1 | 4/2005 | Chiang | |
| 2005/0113905 A1 * | 5/2005 | Greenberg et al. | 623/1.16 |
| 2005/0131516 A1 | 6/2005 | Greenhalgh | |
| 2005/0154446 A1 | 7/2005 | Phillips et al. | |
| 2005/0159803 A1 | 7/2005 | Lad et al. | |
| 2005/0222671 A1 * | 10/2005 | Schaeffer et al. | 623/1.15 |
| 2005/0240258 A1 | 10/2005 | Bolduc et al. | |
| 2005/0273155 A1 | 12/2005 | Bahler et al. | |
| 2006/0004433 A1 | 1/2006 | Greenberg et al. | |
| 2006/0004436 A1 | 1/2006 | Amarant et al. | |
| 2006/0052860 A1 | 3/2006 | Gomez et al. | |
| 2006/0100695 A1 * | 5/2006 | Peacock et al. | 623/1.42 |
| 2006/0161243 A1 | 7/2006 | Fearnot et al. | |
| 2006/0184228 A1 | 8/2006 | Khoury | |
| 2006/0190070 A1 | 8/2006 | Dieck et al. | |
| 2006/0190075 A1 * | 8/2006 | Jordan et al. | 623/1.23 |
| 2006/0247761 A1 | 11/2006 | Greenberg et al. | |
| 2006/0265063 A1 | 11/2006 | Greenhalgh et al. | |
| 2006/0267247 A1 * | 11/2006 | Anukhin et al. | 264/320 |
| 2007/0027525 A1 | 2/2007 | Ben-Muvhar | |
| 2007/0043425 A1 | 2/2007 | Hartley et al. | |
| 2007/0055345 A1 | 3/2007 | Arbefeuille | |
| 2007/0055347 A1 | 3/2007 | Arbefeuille | |
| 2007/0067016 A1 * | 3/2007 | Jung | 623/1.16 |
| 2007/0073388 A1 * | 3/2007 | Krolik et al. | 623/1.31 |
| 2007/0135889 A1 * | 6/2007 | Moore et al. | 623/1.13 |
| 2007/0142894 A1 | 6/2007 | Moore et al. | |
| 2007/0162103 A1 | 7/2007 | Case et al. | |
| 2007/0163668 A1 | 7/2007 | Arbefeuille et al. | |
| 2007/0168019 A1 | 7/2007 | Amplatz et al. | |
| 2007/0179592 A1 | 8/2007 | Schaeffer | |
| 2007/0185560 A1 | 8/2007 | Roeder et al. | |
| 2007/0191927 A1 * | 8/2007 | Bowe et al. | 623/1.15 |
| 2007/0203566 A1 * | 8/2007 | Arbefeuille et al. | 623/1.13 |
| 2007/0208256 A1 | 9/2007 | Marilla | |
| 2007/0219620 A1 | 9/2007 | Eells et al. | |
| 2007/0219624 A1 | 9/2007 | Brown et al. | |
| 2007/0225797 A1 | 9/2007 | Krivoruhko | |
| 2007/0233220 A1 | 10/2007 | Greenan | |
| 2007/0244547 A1 | 10/2007 | Greenan | |
| 2007/0250152 A1 | 10/2007 | Xiao et al. | |
| 2007/0282433 A1 * | 12/2007 | Limon et al. | 623/1.38 |
| 2008/0033527 A1 | 2/2008 | Nunez et al. | |
| 2008/0039920 A1 | 2/2008 | Peacock et al. | |

(56) References Cited

U.S. PATENT DOCUMENTS

| | | | |
|---|---|---|---|
| 2008/0086190 A1* | 4/2008 | Ta | 623/1.11 |
| 2008/0109066 A1 | 5/2008 | Quinn | |
| 2008/0114441 A1 | 5/2008 | Rust et al. | |
| 2008/0114445 A1 | 5/2008 | Melsheimer et al. | |
| 2008/0119943 A1* | 5/2008 | Armstrong et al. | 623/23.7 |
| 2008/0140178 A1 | 6/2008 | Rasmussen et al. | |
| 2008/0195191 A1 | 8/2008 | Luo et al. | |
| 2008/0269866 A1 | 10/2008 | Hamer et al. | |
| 2008/0281399 A1 | 11/2008 | Hartley et al. | |
| 2008/0319534 A1* | 12/2008 | Birdsall et al. | 623/1.22 |
| 2009/0005856 A1* | 1/2009 | Pappas et al. | 623/1.16 |
| 2009/0043376 A1 | 2/2009 | Hamer et al. | |
| 2009/0048663 A1 | 2/2009 | Greenberg | |
| 2009/0090834 A1 | 4/2009 | Chiang | |
| 2009/0105809 A1* | 4/2009 | Lee et al. | 623/1.17 |
| 2009/0138072 A1 | 5/2009 | Gendreau | |
| 2009/0149946 A1 | 6/2009 | Dixon | |
| 2009/0171437 A1 | 7/2009 | Brocker et al. | |
| 2009/0177270 A1 | 7/2009 | Agnew et al. | |
| 2009/0306763 A1 | 12/2009 | Roeder et al. | |
| 2010/0268318 A1 | 10/2010 | Glynn | |
| 2012/0029624 A1 | 2/2012 | Dierking et al. | |
| 2012/0239136 A1 | 9/2012 | Bruzzi | |
| 2012/0323307 A1 | 12/2012 | Richter | |

FOREIGN PATENT DOCUMENTS

| | | |
|---|---|---|
| EP | 1372530 | 2/2006 |
| EP | 1372534 | 11/2006 |
| EP | 1545396 | 12/2008 |
| EP | 1839624 | 6/2014 |
| JP | 2005-512675 | 5/2005 |
| JP | 2009-525139 | 7/2009 |
| KR | 772472 | 11/2007 |
| WO | WO97/21403 | 6/1997 |
| WO | WO03/053288 | 7/2003 |
| WO | WO2005/034810 | 4/2005 |
| WO | WO2005/099628 | 10/2005 |
| WO | WO2006/028925 | 3/2006 |
| WO | WO2007/092276 | 8/2007 |
| WO | WO2007/095283 | 8/2007 |
| WO | WO2007/098937 | 9/2007 |
| WO | WO2008/066923 | 6/2008 |
| WO | WO2009/020653 | 2/2009 |
| WO | WO2010/024879 | 3/2010 |
| WO | WO2010/062355 | 6/2010 |

OTHER PUBLICATIONS

Response to Office Action for U.S. Appl. No. 12/622,351, filed Mar. 9, 2011, 15 pgs.
Office Action for U.S. Appl. No. 12/472,082 dated Oct. 4, 2010, 10 pgs.
Response to Office Action for U.S. Appl. No. 12/472,082, filed Mar. 4, 2011, 14 pgs.
Office Action mailed Nov. 5, 2013 for Japanese Patent Application No. 2010-540640, 7 pgs. Including English translation.
Final Office Action for U.S. Appl. No. 12/622,351 dated Jun. 10, 2011, 12 pgs.
Applicant Initiated Interview Summary for U.S. Appl. No. 12/622,351 dated Nov. 10, 2011, 6 pgs.
Office Action for U.S. Appl. No. 12/622,351 dated Dec. 1, 2011, 16 pgs.
Interview Summary for U.S. Appl. No. 12/622,351 dated Jan. 24, 2012, 2pgs.
Amendment and Response for U.S. Appl. No. 12/622,351 dated Apr. 17, 2012, 11 pgs.
Office Action for U.S. Appl. No. 12/622,351 dated Jun. 27, 2012, 26 pgs.
Applicant Initiated Interview Request Form for U.S. Appl. No. 12/622,351 filed Nov. 2, 2012, 1 pg.
Applicant Initiated Interview Summary for U.S. Appl. No. 12/622,351 dated Nov. 8, 2012, 4 pgs.
Office Action Appendix for U.S. Appl. No. 12/622,351 dated Nov. 8, 2012, 3 pgs.
Amendment and response for U.S. Appl. No. 12/622,351 dated Dec. 26, 2012, 10 pgs.
Office Action for U.S. Appl. No. 12/622,351 dated Apr. 3, 2013, 29 pgs.
Applicant Initiated Interview Summary for U.S. Appl. No. 12/622,351 dated Jun. 11, 2013, 4 pgs.
Miscellaneous Communication for U.S. Appl. No. 12/622,351 dated Jun. 19, 2013, 4 pgs.
Office Action for U.S. Appl. No. 12/472,082 dated Jun. 2, 2011, 13 pgs.
Applicant Initiated Interview Summary for U.S. Appl. No. 12/472,082 dated Nov. 9, 2011, 5 pgs.
Office Action for U.S. Appl. No. 12/472,082 dated Dec. 2, 2011, 14 pgs.
Applicant Summary of Interview for U.S. Appl. No. 12/472,082 dated Jan. 24, 2012, 2 pgs.
Amendment for U.S. Appl. No. 12/472,082 dated Apr. 17, 2012, 10 pgs.
Final Office Action for U.S. Appl. No. 12/472,082 dated Sep. 13, 2012, 15 pgs.
Applicant Summary of Interview for U.S. Appl. No. 12/472,082 dated Feb. 11, 2013, 2 pgs.
Amendment for U.S. Appl. No. 12/472,082 dated Mar. 4, 2013, 9 pgs.
Applicant Initiated Interview Summary for U.S. Appl. No. 12/472,082 dated Mar. 5, 2013, 3 pgs.
Request for Continued Examination for U.S. Appl. No. 12/472,082 dated Mar. 12, 2013, 2 pgs.
Notice of Allowance for U.S. Appl. No. 12/472,082 dated Jun. 21, 2013, 14 pgs.
Search Report for EP12275202 dated Apr. 9, 2013, 8 pgs.
International Search Report for PCT/US2008/013738 dated Feb. 19, 2009, 2 pages.
Written Opinion for PCT/US2008/013738 dated Jun. 26, 2010, 5 pages.
International Preliminary Report on Patentability for PCT/US2008/013738 dated Jun. 26, 2010, 13 pages.
Examination Report No. 1 for Australian Patent Application Serial No. 2008341104 dated Oct. 16, 2012, 3 pages.
Examination Report No. 2 for Australian Patent Application Serial No. 2008341104 dated Jul. 9, 2013, 3 pages.
Examination Report for European Patent Application Serial No. 08 864 911.6 dated Aug. 8, 2012, 4 pages.
Examination Report for European Patent Application Serial No. 08 864 911.6 dated Sep. 1, 2013, 4 pages.
Examination Report for European Patent Application Serial No. 08 864 911.6 dated Nov. 10, 2014, 3 pages.
Notice of Grounds of Rejection for Japanese Patent Application Serial No. 2010-540640 dated Nov. 20, 2012, 8 pages.
Notice of Grounds of Rejection for Japanese Patent Application Serial No. 2010-540640 dated Nov. 5, 2013, 4 pages.
Partial Search Report for European Patent Application Serial No. 11 174 880.2 dated Aug. 8, 2012, 5 pages.
Extended Search Report for European Patent Application Serial No. 11 174 880.2 dated Feb. 8, 2013, 9 pages.
Examination Report for European Patent Application Serial No. 11 174 880.2 dated Sep. 2, 2014, 4 pages.
International Search Report for PCT/US2011/056365 dated Jul. 18, 2012, 5 pages.
Written Opinion for PCT/US2011/056365 dated Apr. 14, 2013, 6 pages.
International Preliminary Report on Patentability for PCT/US2011/056365 dated Apr. 16, 2013, 7 pages.
Extended Search Report for European Patent Application No. 12275202.5 Apr. 9, 2013, 8 pages.
Search Report for Great Britain Patent Application No. 0920327.4 dated Feb. 9, 2011, 1 page.
Combined Search and Examination Report for Great Britain Patent Application Serial No. 0920235.9 dated Mar. 16, 2010, 3 pages.
Examination Report for Great Britain Patent Application Serial No. 0920235.9 dated Jun. 14, 2010, 2 pages.

(56) References Cited

OTHER PUBLICATIONS

International Search Report for PCT/US2010/056673 dated May 26, 2011, 6 pages.
Written Opinion for PCT/US2010/056673 dated May 18, 2012 dated May 18, 2012, 8 pages.
International Preliminary Report on Patentability for PCT/US2010/056673 dated May 22, 2012, 9 pages.
Examination Report No. 1 for Australian Patent Application Serial No. 2010322201 dated Jun. 25, 2013, 4 pages.
Examination Report No. 2 for Australian Patent Application Serial No. 2010322201 dated Aug. 7, 2013, 6 pages.
Examination Report for European Patent Application Serial No. 10 779 432.3 dated May 4, 2012, 4 pages.
Notification of Reason for Rejection for Japanese Patent Application Serial No. 2012-539958 dated Jun. 3, 2014, 2 pages.
Office Action for U.S. Appl. No. 12/904,452 dated May 15, 2012, 12 pages.
Office Action for U.S. Appl. No. 12/904,452 dated Dec. 19, 2012, 11 pages.
Office Action for U.S. Appl. No. 12/904,452 dated May 1, 2014, 11 pages.
Advisory Action for U.S. Appl. No. 12/904,452 dated Jun. 13, 2014, 2 pages.
Notice of Allowance for U.S. Appl. No. 12/904,452 dated Mar. 9, 2015, 5 pages.
Office Action for U.S. Appl. No. 12/472,082 dated Oct. 4, 2010, 9 pages.
Office Action for U.S. Appl. No. 12/472,082 dated Jun. 2, 2011, 13 pages.
Office Action for U.S. Appl. No. 12/472,082 dated Dec. 2, 2011, 14 pages.
Office Action for U.S. Appl. No. 12/472,082 dated Sep. 13, 2012, 15 pages.
Notice of Allowance for U.S. Appl. No. 12/472,082 dated Jun. 21, 2013, 14 pages.
Notice of Allowance for U.S. Appl. No. 12/472,082 dated Aug. 14, 2013, 4 pages.
Office Action for U.S. Appl. No. 12/622,351, dated Oct. 6, 2010, 11 pages.
Office Action for U.S. Appl. No. 12/622,351, dated Jun. 10, 2011, 12 pages.
Office Action for U.S. Appl. No. 12/622,351, dated Dec. 1, 2011, 16 pages.
Office Action for U.S. Appl. No. 12/622,351, dated Jun. 27, 2012, 26 pages.
Office Action for U.S. Appl. No. 12/622,351, dated Apr. 3, 2013, 29 pages.
Notice of Allowance for U.S. Appl. No. 12/622,351, dated Sep. 4, 2013, 8 pages.
Notice of Allowance for U.S. Appl. No. 12/622,351, dated Jan. 21, 2014, 7 pages.
Office Action for U.S. Appl. No. 12/841,807 dated Feb. 24, 2012, 9 pages.
Office Action for U.S. Appl. No. 12/841,807 dated Jun. 7, 2012, 10 pages.
Office Action for U.S. Appl. No. 12/841,807 dated Jan. 11, 2013, 10 pages.
Office Action for U.S. Appl. No. 12/841,807 dated Jul. 31, 2014, 11 pages.
Notice of Allowance for U.S. Appl. No. 12/841,807 dated Nov. 24, 2014, 7 pages.
Office Action for U.S. Appl. No. 12/945,097 dated Feb. 29, 2012, 15 pages.
Office Action for U.S. Appl. No. 12/945,097 dated Dec. 26, 2012, 12 pages.
Office Action for U.S. Appl. No. 12/945,097 dated Oct. 6, 2014, 18 pages.
Office Action for U.S. Appl. No. 12/946,233, dated Aug. 16, 2012, 19 pages.
Office Action for U.S. Appl. No. 12/946,233, dated May 7, 2013, 23 pages.
Office Action for U.S. Appl. No. 12/946,233, dated Apr. 25, 2014, 13 pages.
Office Action for U.S. Appl. No. 12/946,233, dated Aug. 29, 2014, 13 pages.
Office Action for U.S. Appl. No. 12/946,233, dated Feb. 24, 2015, 13 pages.
Office Action for U.S. Appl. No. 12/946,238 dated Feb. 29, 2012, 15 pages.
Office Action for U.S. Appl. No. 12/946,238 dated Sep. 12, 2012, 16 pages.
Office Action for U.S. Appl. No. 12/946,238 dated Oct. 6, 2014, 13 pages.
Office Action for U.S. Appl. No. 13/335,142 dated Feb. 14, 2013, 17 pages.
Notice of Allowance for U.S. Appl. No. 13/335,142 dated Sep. 23, 2013, 11 pages.
Notice of Allowance for U.S. Appl. No. 13/335,142 dated Jan. 16, 2014, 7 pages.

\* cited by examiner

LOW PROFILE NON-SYMMETRICAL STENT

CROSS-REFERENCE To RELATED APPLICATIONS

This application claims priority to U.S. Provisional Application Ser. No. 61/016,753, filed Dec. 26, 2007, which is incorporated herein by reference in its entirety.

FIELD OF THE INVENTION

The present invention relates generally to stents for use in body vessels to treat medical conditions. In particular, this invention relates to an asymmetric stent having opposing sets of curved apices, where the curved section of one set of apices has a radius of curvature that is greater than the curved section of the other set of apices, and may present a lower profile, better compliance with irregular vascular geometry, and higher sealing forces than conventional stents.

BACKGROUND

Stents may be inserted into an anatomical vessel or duct for various purposes. Stents may maintain or restore patency in a formerly blocked or constricted passageway, for example, following a balloon angioplasty procedure. Other stents may be used for different procedures, for example, stents placed in or about a graft have been used to hold the graft in an open configuration to treat an aneurysm. Additionally, stents coupled to one or both ends of a graft may extend proximally or distally away from the graft to engage a healthy portion of a vessel wall away from a diseased portion of an aneurysm to provide endovascular graft fixation.

Stents may be either self-expanding or balloon-expandable, or they can have characteristics of both types of stents. Various existing self-expanding and balloon-expandable stent designs and configurations comprise generally symmetrical end regions including one or more apices formed of nitinol or another alloy wire formed into a ring. The apices commonly comprise relatively acute bends or present somewhat pointed surfaces, which may facilitate compression of the stent to a relatively small delivery profile due to the tight bend of the apices. Although having this advantage, in some situations, such relatively acute or pointed apices may be undesirable, in particular in vessel anatomies that are curved or tortuous such as, for example, the thoracic aorta.

The thoracic aorta presents a challenging anatomy for stent grafts used to treat thoracic aneurysms or dissections. The thoracic aorta comprises a curve known as the aortic arch, which extends between the ascending thoracic aorta (closet to the heart) and the descending thoracic aorta (which extends toward the abdominal aorta). Thoracic stent grafts are used to exclude thoracic aortic aneurysms. A stent graft's ability to conform to the tortuous anatomy of the aortic arch is a major concern. Current designs sometimes lack the desired sealing ability at the proximal end of the stent graft (closest to the heart). Also, current thoracic devices present a relatively large profile which, with some patients' anatomies may be problematic. Finally, many current stents have relatively acute points that may prevent them from being used in the aortic arch for fear of undesirable interaction with the artery wall after an extended amount of time in the patient.

Therefore, a generally nonsymmetrical stent having at least one relatively rounded apex that is less invasive in an expanded state than stents with more acute apices may alleviate the above problems, while providing an improved compliance to the aortic arch and increased radial force if used as a sealing and/or alignment stent, as well as a desirable ability to be crimped to a readily introducible diameter.

As one particular example, type-A thoracic aortic dissection (TAD-A) is a condition in which the intimal layer of the ascending thoracic aorta develops a tear, allowing blood to flow into the layers of the aortic wall, causing the development of a medial or subintimal hematoma. TAD-A is associated with a strikingly high mortality rate (about one-fourth to one-half of victims die within the first 24-48 hours). The only current treatment for TAD-A is open surgery, where the chest is opened, the aorta is clamped, and a vascular prosthesis is sewn in place. Operative mortality rate for this procedure may be around 10%. Endovascular treatment of TAD-B (which affects the descending thoracic aorta) has been effective in reducing short-term and longer term mortality. Therefore, it is desirable to provide an endovascular device configured to address the anatomic challenges of the thoracic aorta.

SUMMARY

The present invention relates generally to stents for use in body vessels to treat medical conditions. In particular, this invention relates to a stent having opposing sets of curved apices, where the curved section of one set of apices has a radius of curvature that is greater than the curved section of the other set of apices, and may present a lower profile than conventional stents. This configuration present an asymmetrical stent. Specifically, embodiments of the presently-presented stent may maintain a low profile while improving compliance with highly tortuous anatomy (such as, for example, that found in the region of the thoracic aorta and particularly the aortic arch) while providing improved radial sealing force compared to some current devices. In another aspect, the presently-presented stent may provide support and spacing within the larger context of a stent or stent-graft device that will allow, for example, placement of ancillary stents and/or stent-grafts.

In one example, the present invention may include a stent that includes at least one proximal apex and at least one distal apex connected with the proximal apices by a plurality of generally straight portions; where each proximal apex includes a first curved portion and each distal apex comprises a second curved portion; where the first curved portion and the second curved portion each includes at least one radius of curvature, and the radius of curvature of at least one of the proximal apices is greater than the radius of curvature of at least one of the distal apices.

In another example, the present invention may include at least one wire formed into stent including a ring of alternating opposed, generally curved apices where a radius of curvature of a plurality of the apices in a first direction is greater than a radius of curvature of the apices in an opposite direction.

Advantageously, the rounded apices may provide atraumatic contact with a vessel, while the combination of more rounded and less rounded apices provides for a low-profile stent that includes desirable compressibility during introduction and desirable compliance and sealing profiles when deployed in a vessel.

BRIEF DESCRIPTION OF THE DRAWINGS

The invention can be better understood with reference to the following drawings and description. The components in the figures are not necessarily to scale, emphasis instead being placed upon illustrating the principles of the invention. Moreover, in the figures, like referenced numerals designate corresponding parts throughout the different views.

DETAILED DESCRIPTION OF THE PREFERRED EXAMPLES

The present invention relates generally to stents for use in body vessels to treat medical conditions. In particular, this invention relates to a novel asymmetric stent having opposing sets of curved apices, where the curved section of one set of apices has a radius of curvature that is greater than the curved section of the other set of apices, and may present a lower profile than conventional stents. The lower profile may present advantages for use in patients with particularly tortuous or small-diameter vessels.

In the present application, the term "proximal" refers to a direction that is generally closest to the heart during a medical procedure, while the term "distal" refers to a direction that is furthest from the heart during a medical procedure. Reference throughout is made to proximal and distal apices, but those of skill in the art will appreciate that the proximal-distal orientation of stents of the present invention may be reversed without exceeding the scope of the present invention.

As shown in FIGS. 4-15, this novel stent is not symmetrical like many commercially available stents, in that the radius of curvature of the opposing proximal and distal apices is different between the top and bottom of the stent. The stents may be attached to either end of a stent graft to provide sealing and may be used internally or externally to the graft material to provide support to the graft.

The asymmetric stent may be configured such that, when used with a graft, it will provide a sufficiently strong radial force at the graft's end openings to hold the graft material open against the artery wall. Also, the stent is intended to be short in length so that the graft will include flexibility sufficient to accommodate a patient's anatomy. This combination of flexibility and strong radial force provides an improved seal between the graft and artery wall. In addition, enhanced flexibility is provided as well, particularly when one or more stents are used to provide short segments and better accommodate curves.

Figure 1:
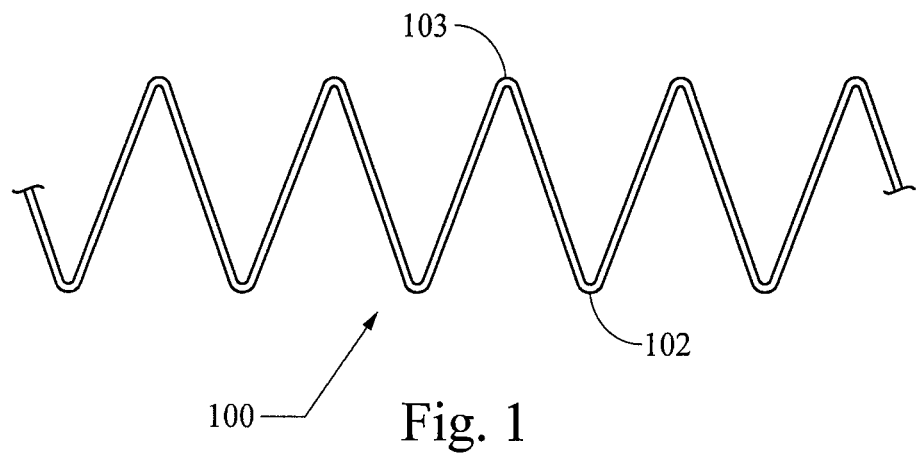
FIGS. 1-3 show different views of a symmetrical stent.
Figure 2:
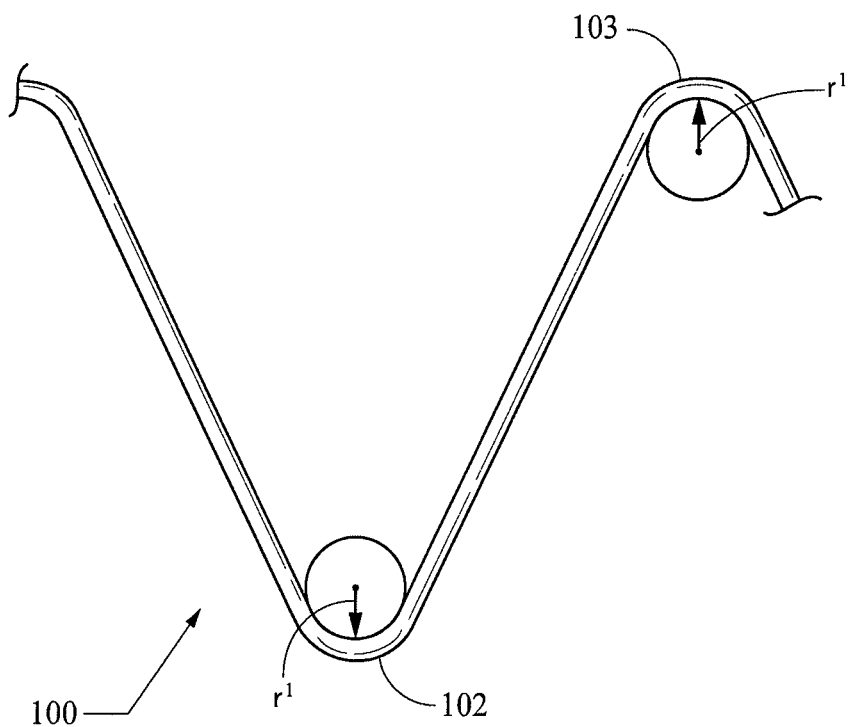
Figure 3:
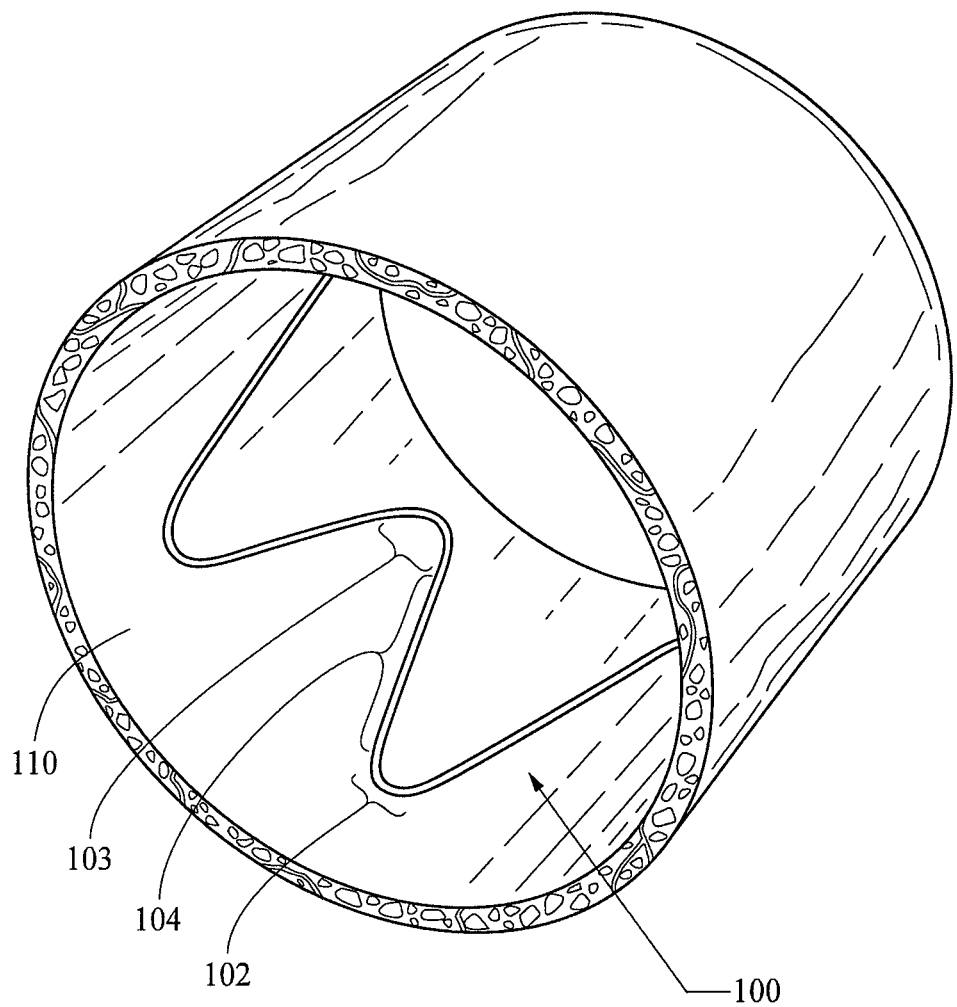

FIG. 1 shows a conventional stent 100, which has symmetrical apices 102, 103. Specifically, the proximal apices 102 and the distal apices 103 all have generally the same radii of curvature ($r^1$), which is illustrated in graphic form in FIG. 2. FIG. 3 is adapted from an FEA contour simulation and shows the stent 100 in a simulated artery 110, where the stent 100 is 20% oversized. The proximal and distal apices 102, 103 (circled) exert little or no pressure against the artery wall 110, while an intermediate region 107 exerts a higher pressure to provide—in one example—a total radial sealing force of 0.178 lbf. This configuration may be crimped to 18 Fr (e.g., for introduction via a catheter), with a maximum bend strain in the apices 102, 103 of about 5.8%. When using, for example, a typical NiTi wire for the stent, it is desirable not to exceed 10-12% strain to avoid increased risk of deforming the wire or adversely affecting its durability.

FIGS. 4-7 show a first example of a non-symmetrical stent 200, which is formed as a wire ring that has non-symmetrical proximal and distal generally curved apex portions (apices) 202, 203 separated from each other by intermediate generally straight portions. Specifically, the distal apices 203 all have generally the same radii of curvature ($r^d$) as each other, but the distal apices' radii of curvature are different from those of the proximal apices 202 ($r^p$). The distal apices 203 (which may be attached to and generally covered by graft material in a stent graft as described below with reference to FIGS. 14-15) are generally narrowly rounded in a manner not dissimilar from a traditional z-stent, but the proximal apices 202 are more broadly rounded. The difference in the proximal and distal apices 202, 203 is illustrated in graphic form in FIG. 5. In the illustrated example, the rounded proximal apices 202 have a radius of curvature of 6.0 mm, while the narrower distal apices 202 have a radius of curvature of 1.0 mm. In certain examples of non-symmetrical stents of the present invention, the radius of curvature of the rounded proximal apices (measured in the manner shown in FIG. 5) may be from about 4 mm to about 9 mm, and the radius of curvature of the narrower distal apices may be from about 0.5 mm to about 1.5 mm.

In these and other examples, the ratio of the proximal apices' radius of curvature to the distal apices' radius of curvature may be about 2.6:1 to about 18:1, and desirably may be about 6:1. The outer circumference of the stent 200 preferably is generally consistent such that, in this configuration, a solid outer face around the stent 200 would form a cylinder, although the stent will most preferably provide compliance with a surface less smooth than a cylinder.

Figure 6:
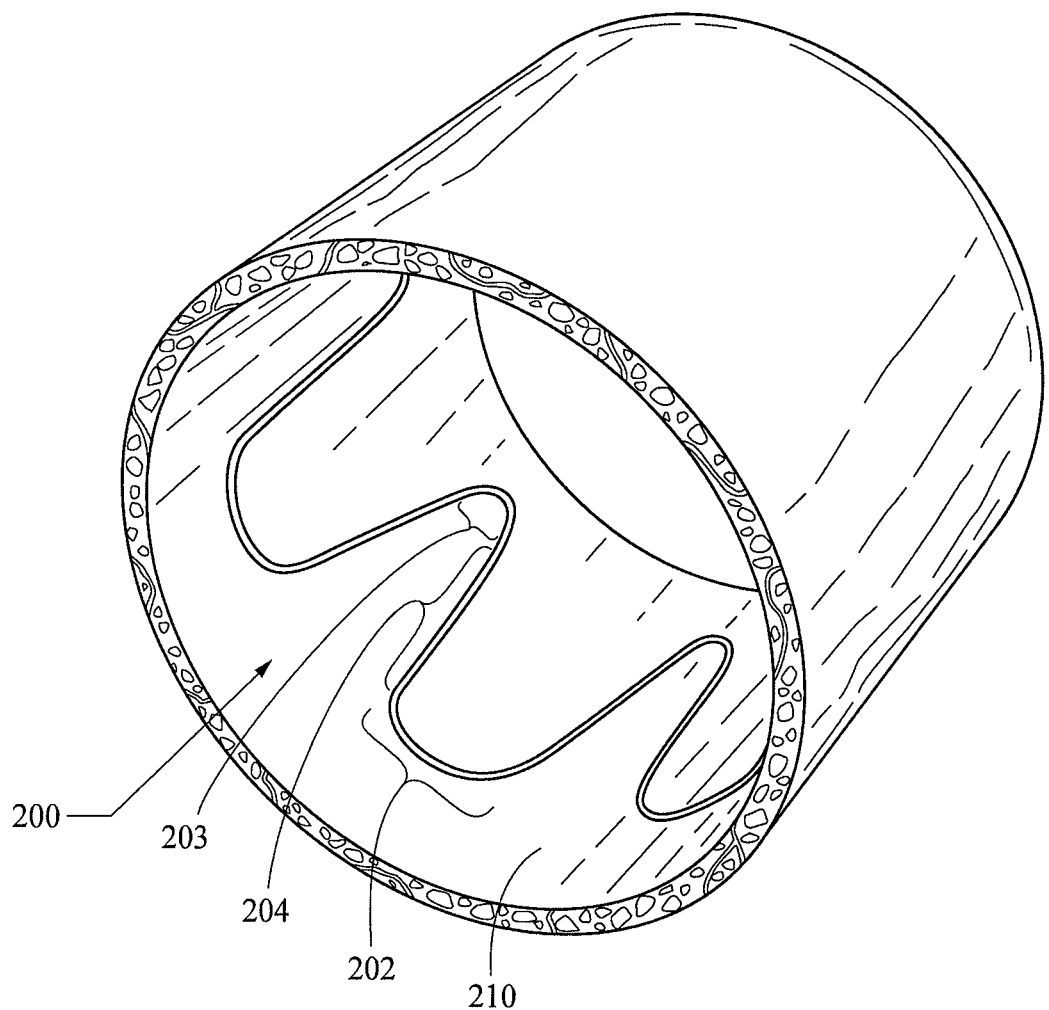
FIG. 6 shows the stent of FIG. 4 in a simulated artery.

FIG. 6 is adapted from an FEA contour simulation and shows the stent 200 in a simulated artery 210, where the stent 200 is 20% oversized. The proximal and distal apices 202, 203 (circled) exert little or no pressure against the artery wall 210, while an intermediate region 204 (boxed) exerts a greater pressure to provide—in the illustrated example—a total radial sealing force of about 0.160 lbf. This configuration may be crimped to 18 Fr, with a maximum bend strain in the apices 202, 203 of about 6.5%.

Figure 4:
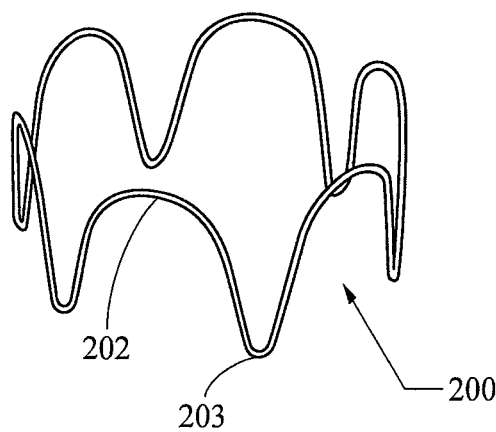
FIG. 4 depicts an example of an asymmetric stent.
Figure 5:
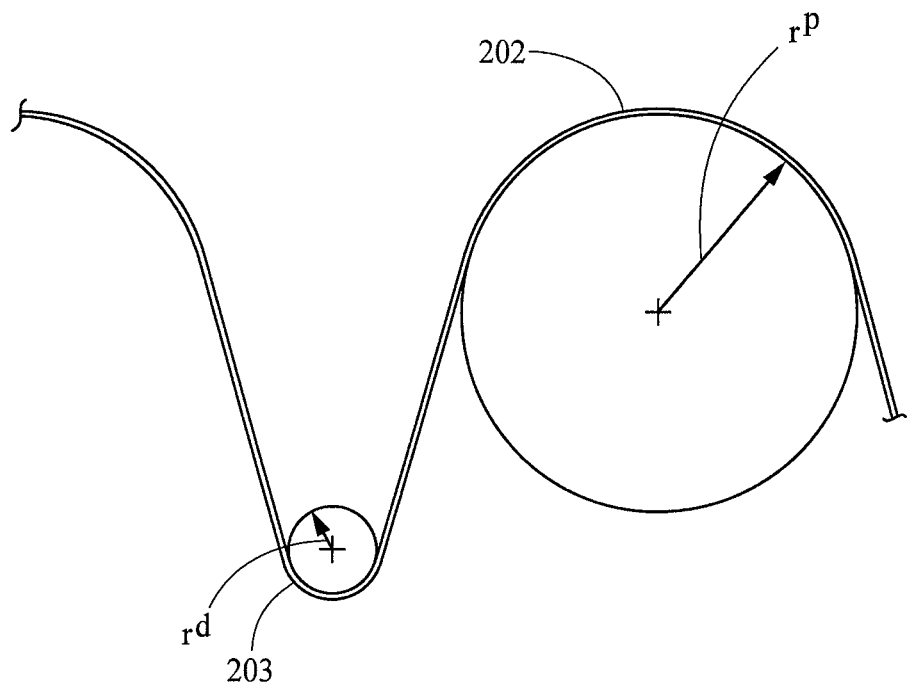
FIG. 5 diagrammatically illustrates the asymmetrical radii of curvature of the stent of FIG. 4.
Figure 7:
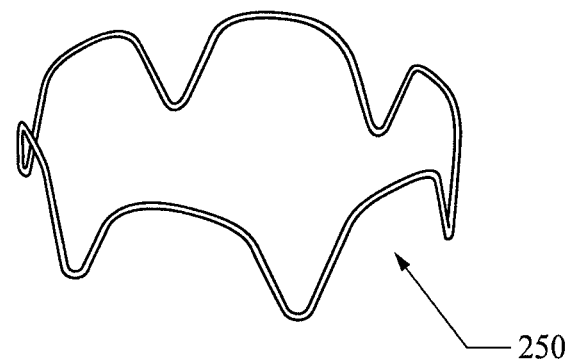
FIG. 7 depicts another example of an asymmetric stent.

FIG. 7 shows another non-symmetrical stent embodiment 250 that is very similar to the embodiment of FIGS. 4-6, but which has a shorter proximal-distal length. Each of the examples shown in FIGS. 4-7 may be manufactured in substantially the same manner as current z-stents, with a modification only of forming the proximal apices to include a greater radius of curvature than the distal apices.

Figure 8:
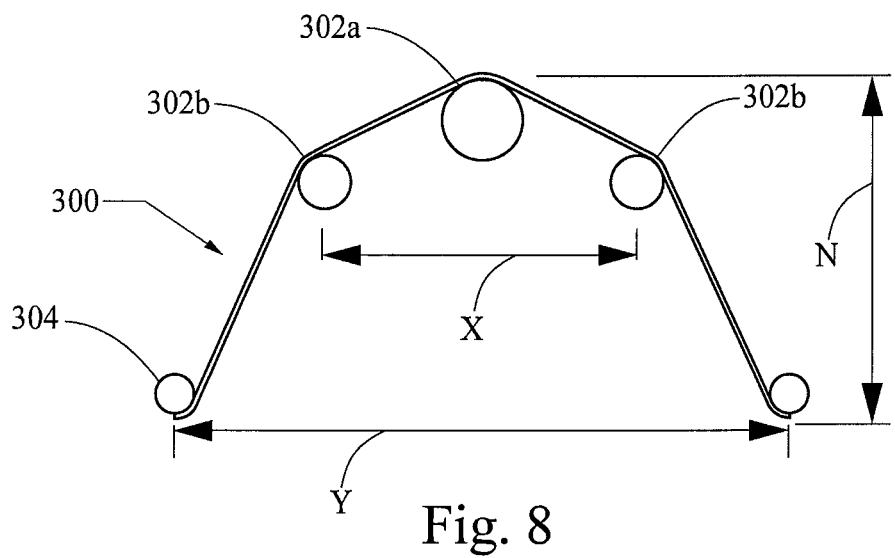
FIG. 8 diagrammatically illustrates the asymmetrical radii of curvature of yet another example of a stent.
Figure 9:
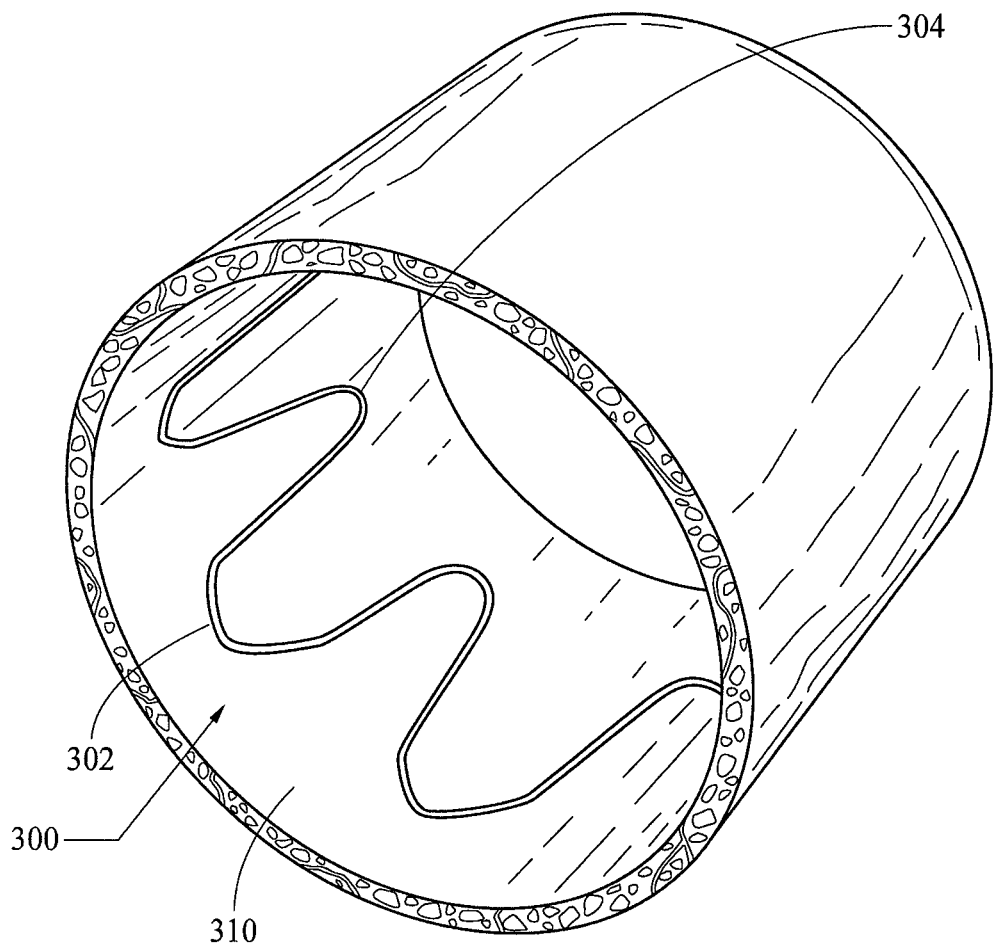
FIG. 9 shows the stent of FIG. 8 in a simulated artery.

FIGS. 8-9 illustrate another example of a non-symmetrical stent 300, which has a proximal "rounded roof shape" profile rather than the generally semicircular profile of the examples described above with reference to FIGS. 4-7. The profile of each proximal apex 302 includes a central fillet 302a and a pair of symmetrically opposed shoulder fillets 302b that may be generally equidistant from the central fillet 302a, or that may be disposed at varied distances therefrom. For the proximal apices of the stent 300, the central fillets 302a each have a radius of curvature of 1.0 mm, and the shoulder fillets 302b each have a fillet radius of curvature of 0.5 mm. The distal apices 304 have a radius of curvature of 1.0 mm. In another example having the rounded roof shape configuration (not shown), the central and shoulder fillets of proximal apices may each have the same radius of curvature such as, for example, 0.5 mm each, with distal apices also having a 0.5 mm radius of curvature. In other examples, the central and shoulder fillets 302a, 302b may each have a radius of curvature from about 0.5 mm to about 5 mm, and the distal apices may each have a radius of curvature of about 0.5 mm to about 1.5 mm. In another example having the rounded roof shape configuration (not shown), the ratio between the radii of curvature of the central and each shoulder fillet of the proximal apices may be about 3:1. FIG. 8 also shows three spans useful for describing desirable proportions in stent embodiments: "x" indicates the distance between the apical extremities of the shoulder fillets 302b, "y" indicates the distance between the tips of the distal apices 304, and "z" indicates the distance along a longitudinal axis between the tip of the distal apices 304 and the apical extremity of the proximal fillet 302a. Desirable embodiments may include an x:y ratio of about 1:3 to about 7:8 and a y:z ratio of about 1:1 to about 3:1. In yet another example (not shown), the filleted apices of this example may be combined with the generally semicircular apices of the example described with reference to FIGS. 4-7.

FIG. 9 is adapted from an FEA contour simulation and shows the stent 300 in a simulated artery 310, where the stent 300 is 20% oversized. The proximal and distal apices 302, 304 exert little or no pressure against the artery wall 310, while an intermediate region exerts a greater pressure to provide—in the illustrated example—a total radial sealing force of about 0.420 lbf. This configuration may be crimped to 18 Fr, with maximum bend strains in the apices that may be less than about 9% and preferably are less than about 10-12%. The greater radial sealing force of this example may provide advantages for stent placement and retention in certain circumstances as compared to existing z-stents.

Figure 10:
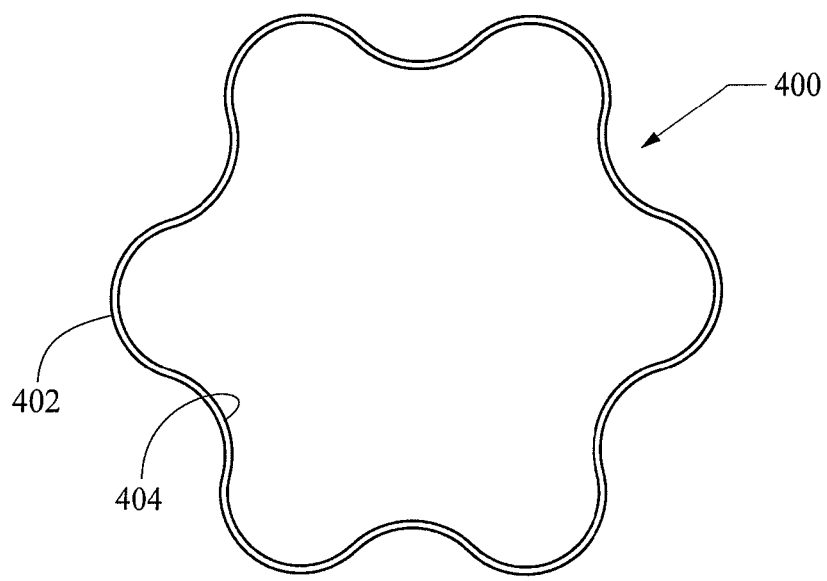
FIG. 10 shows an end view of still another example of an asymmetric stent.
Figure 11:
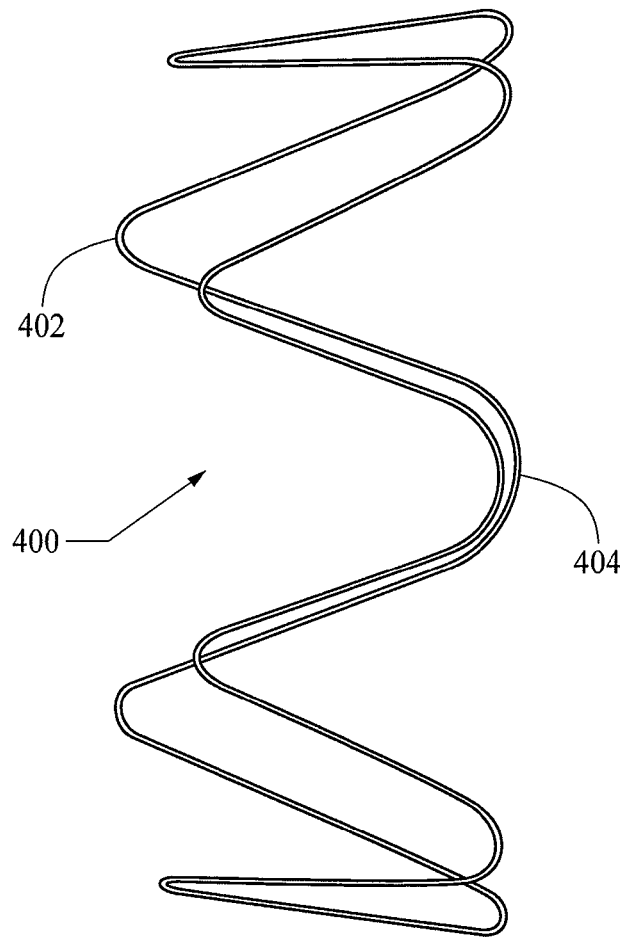
FIG. 11 shows a side view of the stent of FIG. 10.
Figure 12:
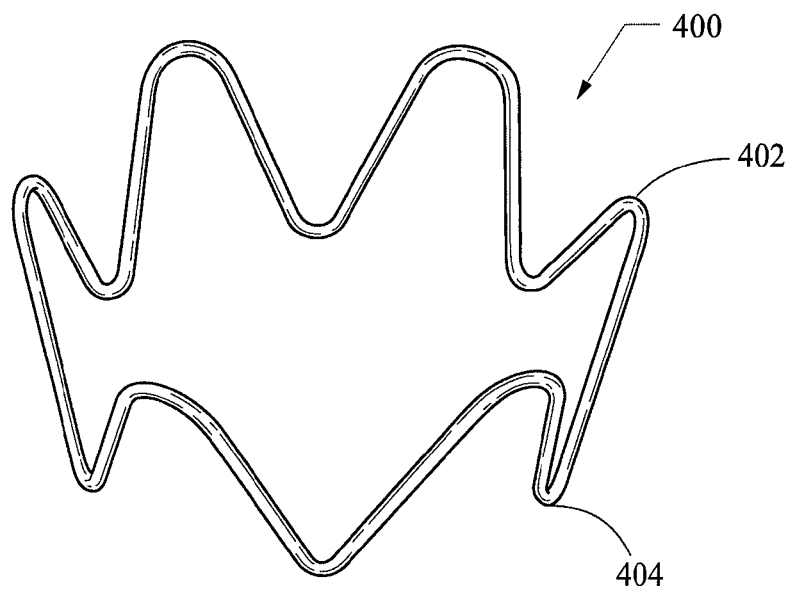
FIG. 12 is a top perspective view of the stent of FIG. 10.

FIGS. 10-13 illustrate another example of a non-symmetrical stent 400, which has an expanded "flower configuration" as shown in FIG. 10. Specifically, when the stent 400 is in an expanded configuration, the circumference around the proximal more-rounded apices 402 is greater than the circumference around the distal less-rounded apices 404, which is shown most clearly in FIGS. 11-14. In this configuration a solid outer face around an expanded stent 400 would form a frustum of a cone. This configuration may be manufactured in the same manner as the examples described above with reference to FIGS. 4-7 (i.e., producing a stent with a generally uniform outer circumference), with an added step that may include drawing the distal apices 404 into a smaller circumference upon suturing them to a smaller diameter graft material. Alternatively, or in addition, the stent 400 may be heat-set to impose the desired shape.

Figure 13:
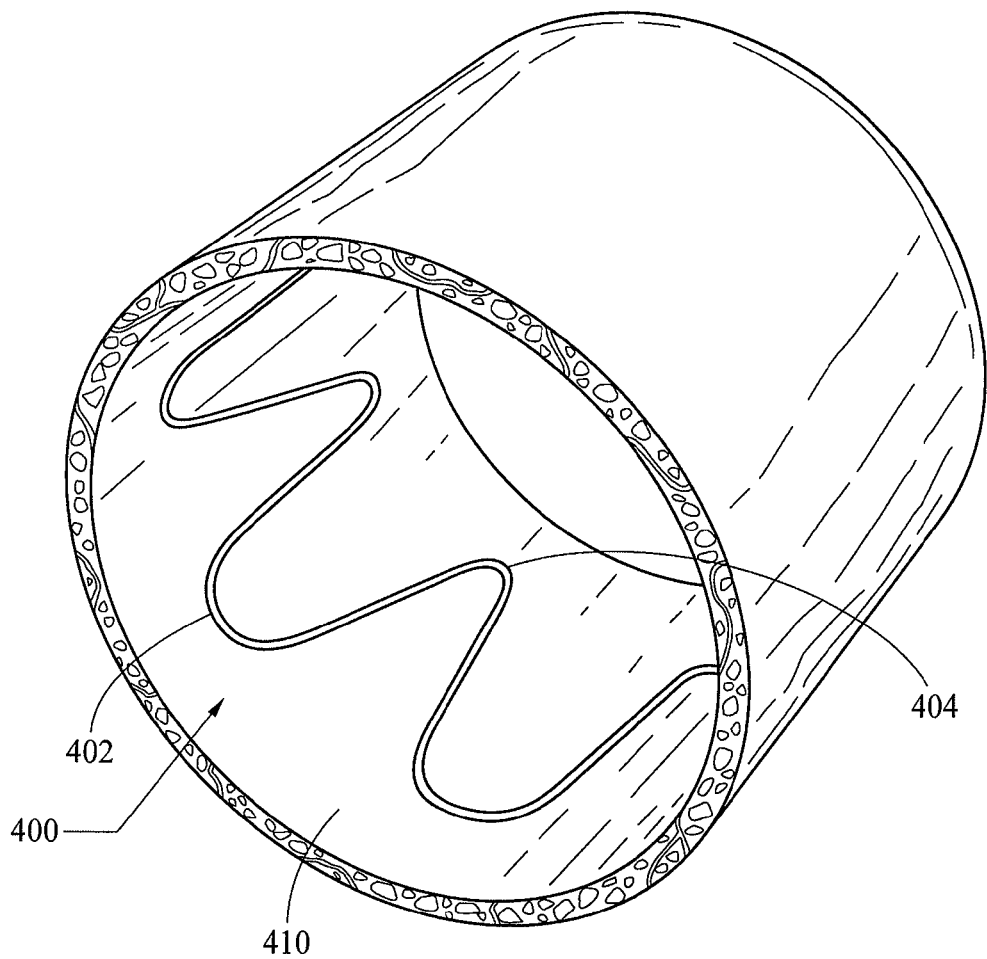
FIG. 13 shows the stent of FIG. 10 in a simulated artery.

FIG. 13 is adapted from an FEA contour simulation and shows the stent 400 in a simulated artery 410, where the stent 400 is 20% oversized. Surprisingly, the contour of pressure distribution along proximal and distal apices 402, 404 as well as an intermediate region is generally uniform throughout the stent circumference. The illustrated configuration provides a total radial sealing force of about 0.187 lbf. This property of generally uniform pressure distribution may provide advantages in certain applications of providing a seal and/or presenting less abrasion of a vessel wall through graft material as compared to stents with less uniform pressure distribution.

Figure 14:
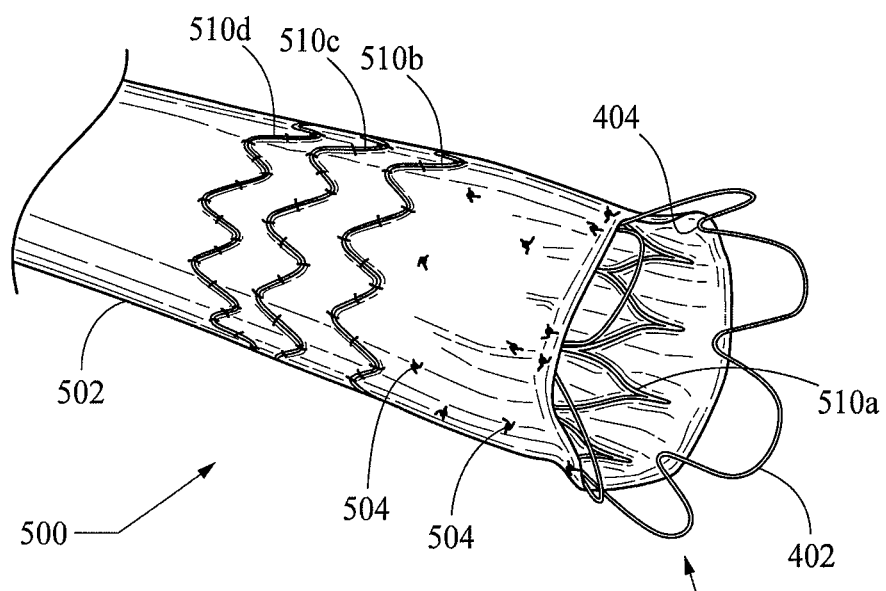
FIG. 14 is a partial perspective of a stent-graft incorporating the stent of FIG. 10.
Figure 15:
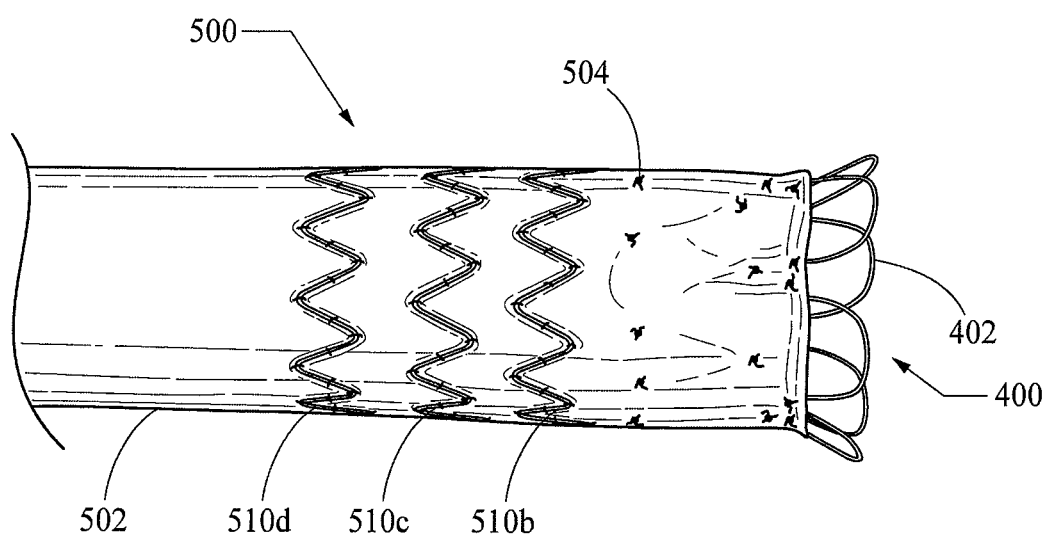
FIG. 15 illustrates a side view of the stent-graft of FIG. 14.

FIGS. 14-15 show two different views of a stent graft 500 using a stent example 400 of the present invention described above with reference to FIGS. 10-13. The stent graft 500 is shown in an expanded state and may be configured for use in treating a thoracic aortic aneurysm. The stent 400 is disposed at the proximal end of a generally cylindrical graft sleeve 502, to which its distal apices 404 are secured by sutures 504. The stent graft 500 also includes a series of z-stents 510a-d disposed distally from the stent 400. The first z-stent 510a is attached to the inner circumference of the graft 502, and the other z-stents 510b-510d are attached to the outer diameter of the graft 502. The proximal end of the stent 400 extends beyond the proximal end of the graft in a manner that may facilitate anchoring the graft in a vessel of a patient (e.g., a blood vessel).

The rounded points on the stent may protrude from the graft material only a small amount as is shown in FIGS. 14-15. In this example, only a small portion of the bare wire will be exposed to the artery wall. These unique (larger radii) rounded points are far less likely to perforate the artery wall than sharper points of a different stent configuration. Advantageously, this asymmetric stent design will maximize the efficacy of the seal while preserving the condition of the artery wall. Specifically, the narrower stent apices will provide for desirable radial expansion/ sealing force, and the broader rounded apices will provide for a desirably atraumatic contact with an artery wall.

Figure 16:
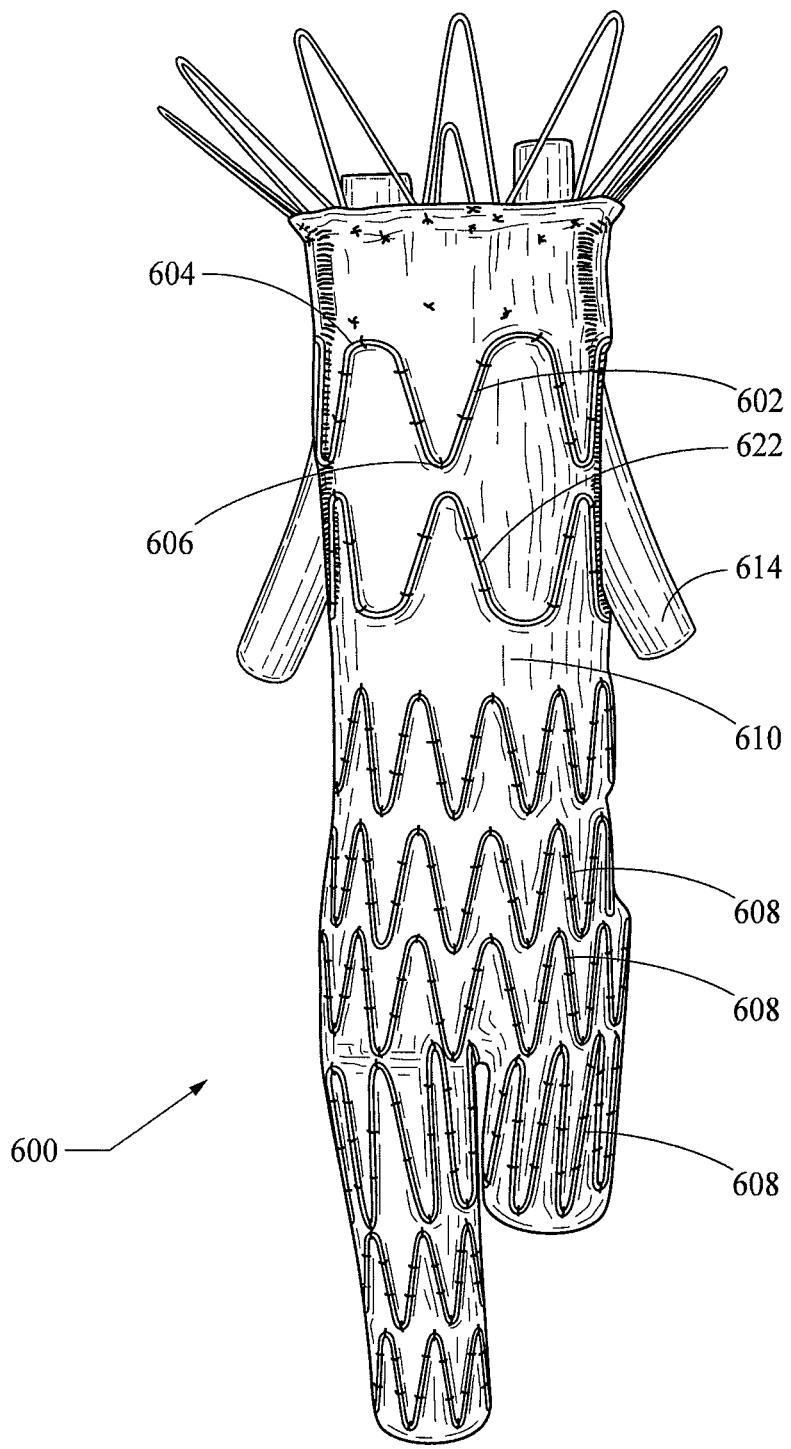
FIGS. 16-18 show a stent-graft with side branches.
Figure 17:
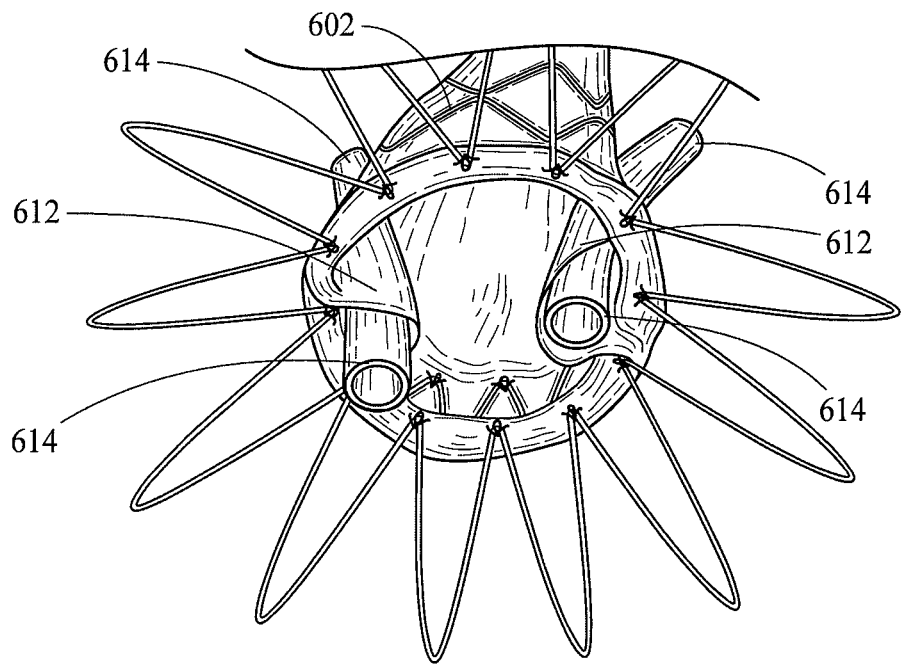
Figure 18:
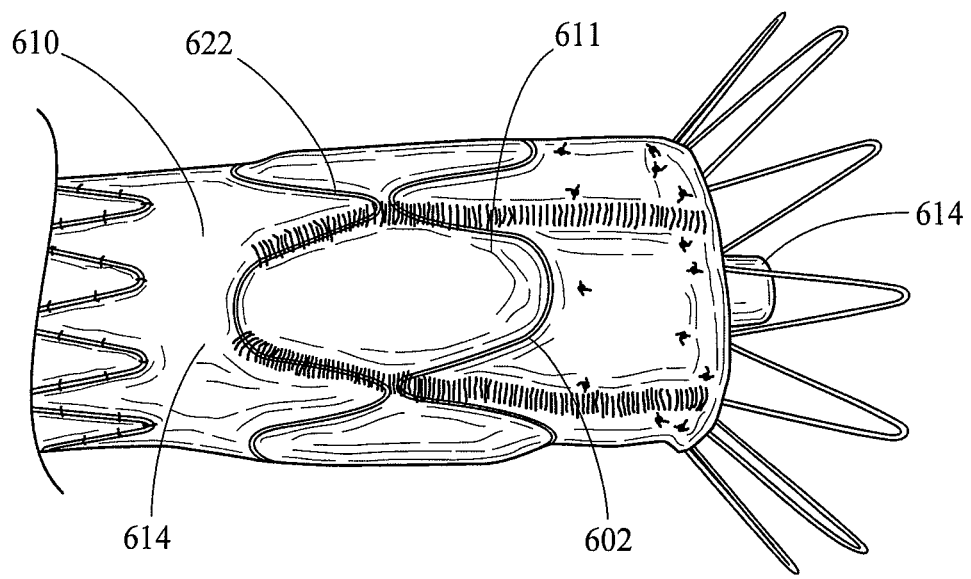

FIGS. 16-18 show a stent-graft embodiment 600 that includes a non-symmetrical stent 602 having more broadly rounded proximal apices 604 and more narrowly rounded distal apices 606. The stent 602 is attached by sutures to the inner surface (not shown) or outer surface of a generally columnar graft 610, which includes other stents 608. A second layer of graft material 612 is also attached to the inner circumference of the graft 610 midway down its length and extends proximally through the inner circumference of the stent 602.

As shown in the end view of FIG. 17, this construction provides a passage for branch structures 614 (that may be embodied, for example, as tubular or non-tubular stents, stent-grafts, shown here for the sake of illustration as generic tubular structures), which pass through the passage formed between the two layers 610, 612 and through an aperture 611 in the graft 610. The tubular structures 614 will advantageously be disposed generally transversely through the inner radius of the more broadly rounded proximal apices 604 of the stent 602, which provides atraumatic columnar support for the graft 610 as well as an anchor for the tubular structures 614. The stent-graft 600 may be particularly useful for treatment of an abdominal aortic aneurysm (AAA) that is immediately adjacent to, or that goes across, the renal arteries such that it has a short neck and lacks a contact area that is sufficient to create an effective proximal seal and avoid the proximal Type I endoleaks that may occur with some currently-available AAA stent-grafts. Those of skill in the art will appreciate that the stent-graft 600 will allow general occlusion of the AAA, while providing patent passage through the descending aorta and from the aorta to the renal arteries. Specifically, a stent-graft configured in the manner of the stent-graft embodiment 600, which includes a modular design that may include branch stents and/or stent-grafts, will allow a seal to be formed above the renal arteries and below the celiac and superior mesenteric arteries. Also, as shown in FIG. 16, a second non-symmetrical stent 622 may be placed adjacent the first non-symmetrical stent 602 in an opposite orientation that will provide additional atraumatic support for the branching tubular structures 614.

Figure 19:
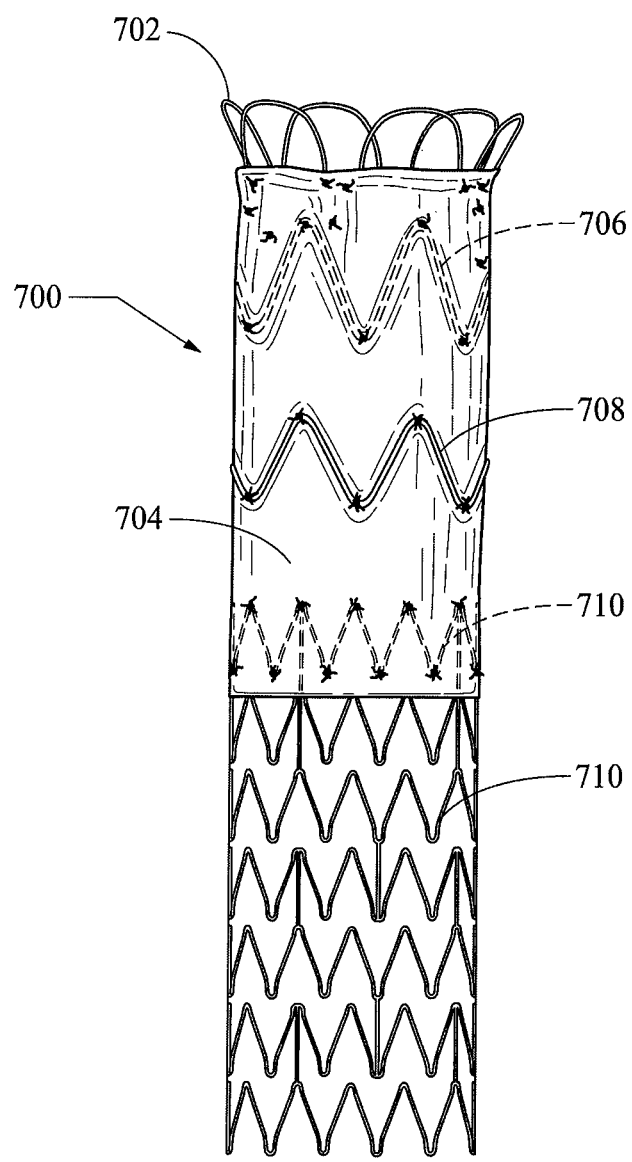
FIG. 19 is a side view of a stent-graft device configured for endovascular treatment of a thoracic aorta dissection.

FIG. 19 shows a stent-graft device 700 configured for endovascular treatment of a thoracic aorta dissection. The device 700 includes a non-symmetrical alignment stent 702 attached to a first end of a tubular graft material 704. A sealing stent 706 is attached in the central lumenal graft space proximate the alignment stent 702. The sealing stent 706 preferably is configured with a high radial force to promote efficacious sealing of the graft material 704 against a vessel wall. A body stent 708 configured here as a z-stent is disposed on the exterior of the graft material 704 and preferably is configured to provide longitudinal and circumferential stability/ columnar support for the graft material of the device 700, such that it will conform to the vasculature and resist buckling when deployed in torturous anatomy such as the ascending thoracic aorta. A bare cannula stent 710 (such as, for example, a cut nitinol stent) is attached in the tubular graft material 704 at the opposite end from the alignment stent 702. This cannula stent 710 preferably is a conformable kink-resistant stent that provides distal sealing and migration-resistance. In a deployment of the device 700 to treat an aortic dissection, the alignment stent 702 preferably will be disposed proximal (nearer the heart) relative to the vessel tear, with the graft material traversing the tear in a manner generally sealing it from blood flow. And, the distal cannula stent 710 will help conform to the vasculature and retain a seal for treatment of the dissection. One or more of the sealing stent 706, body stent 708, and bare stent 710 may include one or more barbed projections configured to help anchor the device 700.

Stent examples of the present invention may be constructed of NiTi alloys or other materials presently known or yet to be developed, all within the scope of the present invention. The stents preferably are made from Nitinol wire and will therefore be MRI compatible. In another preferable embodiment, a stent may be made from a laser-cut Nitinol cannula, effectively rending it a seamless or nearly-seamless wire-like construction. Nitinol's superelastic properties will facilitate the stents ability to be crimped down into a low profile delivery system.

Although various examples of the invention have been described, the invention is not to be restricted except in light of the attached claims and their equivalents. Moreover, the advantages described herein are not necessarily the only advantages of the invention and it is not necessarily expected that every example of the invention will achieve all of the advantages described. Different embodiments not expressly described herein including those with features combined in a different manner than expressly illustrated herein may be practiced within the scope of the present invention. For at least these reasons, this narrative description should not be construed as defining the invention; rather, the claims set forth and define the present invention.

We claim:

1. A stent comprising:
   at least one distal apex comprising
      first and second generally straight portions and
      a first curved portion disposed between the first and second straight portions and comprising a first radius of curvature; and
   at least one proximal apex comprising
      third and fourth generally straight portions and
      a second curved portion disposed between the third and fourth straight portions and comprising a second radius of curvature that is greater than the first radius of curvature, and
   where at least one of the first and second generally straight portions is continuous with at least one of the third and fourth generally straight portions,
   where the first radius of curvature is from about 0.5 mm to about 1.5 mm,
   where the second radius of curvature is from about 4 mm to about 9 mm,
   where a ratio of the first radius of curvature to the second radius of curvature is about 1:2.6 to about 1:18, and
   where the stent comprises at least one uncovered region.

2. The stent of claim 1 comprising a generally continuous plurality of proximal and distal apices, the outer surfaces of which define a cylinder having a generally consistent circumference.

3. The stent of claim 1 where the first radius of curvature is about 1 mm, and the second radius of curvature is about 6 mm.

4. The stent of claim 1 where each of the proximal apices are circumferentially offset from the distal apices.

5. The stent of claim 1 comprising a generally continuous plurality of proximal and distal apices, the outer surfaces of which define a frustum of a cone.

6. The stent of claim 5, further comprising a graft, where at least one distal apex of the stent is attached to the graft using one or more sutures.

7. The stent of claim 1 where at least one of the proximal apices comprises first and second fillets disposed a distance from the second curved portion, the first fillet comprising a first fillet radius of curvature and the second fillet comprising a second fillet radius of curvature.

8. The stent of claim 7 where the first fillet radius of curvature and the second fillet radius of curvature each have a radius of curvature of about 1 mm, and the first curved portion has a radius of curvature of about 0.5 mm.

9. The stent of claim 7 where the ratio of the radius of curvature of the first curved portion to at least one of the first and second fillet radius of curvature is about 1:1 to about 1:10.

10. The stent of claim 7, further comprising a graft, where at least one distal apex of the stent is attached to the graft using one or more sutures.

11. The stent of claim 1,
   where the stent includes a wire having the curved and the straight portions and generally defining a cylinder;
   where the first radius of curvature is about 1 mm; and the second radius of curvature is about 6 mm.

12. A stent comprising:
   a plurality of proximal apices and a plurality of distal apices connected with the proximal apices by a plurality of generally straight portions;
   where each proximal apex comprises a first curved portion and each distal apex comprises a second curved portion;
   where the first curved portion and the second curved portion each comprises at least one radius of curvature, and the radius of curvature of at least one of the proximal apices is greater than the radius of curvature of at least one of the distal apices,
   where the radius of curvature of the distal apices is from about 0.5 mm to about 1.5 mm,
   where the radius of curvature of the proximal apices is from about 4 mm to about 9 mm, and
   where a ratio of the radius of curvature of the distal apices to the radius of curvature of the proximal apices is about 1:2.6 to about 1:18, and
   where the stent comprises at least one uncovered region.

13. The stent of claim 12 where an outer circumference around the proximal apices is greater than an outer circumference around the distal apices.

14. The stent of claim 12, further comprising a graft, where at least one distal apex of the stent is attached to the graft using one or more sutures.

15. The stent of claim 14, further comprising at least one branch stent, at least one branch graft, or at least one branch stent-graft, a portion of which is at least disposed transversely through an inner radius of a proximal apex.

16. The stent of claim 14, further comprising a second stent attached to the graft, where the second stent comprises plurality of proximal apices and a plurality of distal apices connected with the proximal apices by a plurality of generally straight portions;
> where each proximal apex comprises a first curved portion and each distal apex comprises a second curved portion;
> where the first curved portion and the second curved portion each comprises at least one radius of curvature, and the radius of curvature of at least one of the distal apices is greater than the radius of curvature of at least one of the proximal apices.

17. The stent of claim 14, further comprising a bare stent attached to and extending distally from the graft.

18. The stent of claim 17, further comprising at least one stent attached to and providing columnar support for the graft.

19. The stent of claim 1 where a ratio of the first radius of curvature to the second radius of curvature is about 1:6.

20. The stent of claim 12 where a ratio of the radius of curvature of the distal apices to the radius of curvature of the proximal apices is about 1:6.

* * * * *